United States Patent [19]

Ohno

[11] Patent Number: 4,579,779
[45] Date of Patent: Apr. 1, 1986

[54] METHOD OF ENCAPSULATING VOLATILE ORGANIC LIQUIDS

[75] Inventor: Shigeru Ohno, Kamakura, Japan

[73] Assignee: Freund Industrial Co., Ltd., Tokyo, Japan

[21] Appl. No.: 537,682

[22] Filed: Sep. 30, 1983

[51] Int. Cl.$^4$ .............................................. B01J 13/02
[52] U.S. Cl. ................................... 428/402.2; 239/53; 252/315.1; 252/315.6; 424/14; 264/4.1
[58] Field of Search ...................... 264/4.1; 428/402.2; 424/14; 252/315.1, 315.6; 239/53

[56] References Cited

U.S. PATENT DOCUMENTS 3,393,155 7/1968 Schutte et al. .................... 428/402.2
4,268,411 5/1981 Iwata et al. ...................... 428/402.2

Primary Examiner—Paul Lieberman
Assistant Examiner—Robert A. Wax
Attorney, Agent, or Firm—Kane, Dalsimer, Kane, Sullivan and Kurucz

[57] ABSTRACT

A method of encapsulating organic liquids for controlled volatilization and release is described, which comprises in one embodiment charging a fine silica into a mixing container which does not inflict shearing force to the contents and adding the liquid (having a viscosity of 50 centipoise or less at 25° C.) onto and mixing with the fine silica in the mixing container.

2 Claims, 2 Drawing Figures

METHOD OF ENCAPSULATING VOLATILE ORGANIC LIQUIDS

BACKGROUND OF THE INVENTION

1. Field of the Invention

The invention relates to controlled release compositions and more particularly relates to methods of preparing controlled release compositions such as encapsulated volatile organic liquids.

2. Brief Description of the Invention

The literature is replete with descriptions of prior art methods and techniques for the preparation of devices and compositions which allow for the controlled release of volatile organic liquids. One technique comprises impregnating absorbent particulate solids such as active charcoal, diatomaceous earth, clay, aluminum silicates, silica and like materials with the organic liquid. Over a period of time, the organic liquid vaporizes and is released from the absorbent carrier.

The prior art technique of employing absorbent solid particle carriers as described above has not been entirely satisfactory. Only limited quantities of the volatile organic liquids can be absorbed by the particulate solid carriers (on the order of 10 percent or less, by weight). Also, above the limited levels of absorbability, the particulate solids become wet and difficult to handle, because they lose the fluidity or flowability associated with granular particles and powders.

By the method of the present invention, particles of amorphous silica are employed to encapsulate volatile organic liquids. The resulting capsule compositions will allow the controlled, slow release of vapors over a period of time. The capsule materials are easy to handle and flow with the fluidity associated with granular or powdery solids.

SUMMARY OF THE INVENTION

The invention comprises a method of encapsulating a volatile organic liquid having a viscosity of 50 centipoise or less at 25° C., with particles of amorphous silica, which comprises;
  providing particles of said silica in a mixing vessel;
  adding said liquid to the particles; and
  mixing the silica and the liquid under non-shearing conditions.

DETAILED DESCRIPTION OF THE PREFERRED EMBODIMENTS OF THE INVENTION

The method of the invention is carried out by mixing under non-shear conditions, an amorphous silica with the volatile organic liquid to be encapsulated therein.

The method may be employed to encapsulate any organic liquid having a viscosity of not more than about 50 centipoise (at 25° C.). If a more viscous liquid is used, the resulting composition tends to lose fluidity, even at low levels of loading. However, with the exception of viscosity, there is no limitation on the nature of the liquid to be encapsulated. A mixture of solid and liquid may also be encapsulated as long as the mixture has a viscosity not exceeding about 50 centipoise at 25° C.

The method is advantageous to encapsulate volatile organic liquids or mixtures containing volatile organic liquids, i.e., liquids which are normally vaporized at ambient temperatures and under atmospheric, sub- or super pressures. These organic liquids will vaporize and be released slowly (controlled) from the capsule compositions of the invention.

The silica employed to encapsulate the above-described organic liquids according to the method of the invention is an amorphous silica, and preferably a gel type produced either by the wet or dry production technique, further characterized by having an average particle size of not more than about 300 microns. Most preferred, the silica employed will have an average particle size of 300 micron or less and a micropore distribution characterized by 50% of the integrated volume of said micropore being distributed to the micropores having a radius up to 1000 Angstroms; most preferably up to 500 Angstroms.

The proportions of organic liquid and silica admixed together to encapsulate the liquids may be varied over a wide range, depending on the loading to be obtained.

In carrying out the method of the invention, either batch type or continuous type mixing equipment may be used. For example, mixing vessels, either vertical or horizontal type having ribbon like blades and vertical type mixing vessels having a screw type agitator can be used as long as the blades or an agitator rotate less than 100 r.p.m. The most suitable mixing equipment for carrying out this invention is a mixing vessel which has no agitating means but rotates itself. For example, a V-shaped mixer, a double cone type mixer and inclined rotating cylinder types of mixer are best. Advantageously, the inclined rotating cylinder type of mixer is used for a continuous operation. All of the equipment described above does not mix under high shearing conditions.

Figure 2:
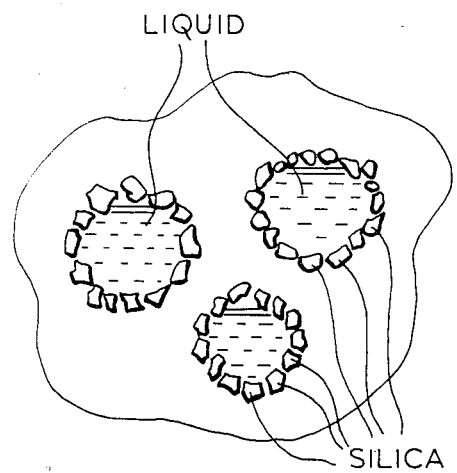
FIG. 2 is a magnified view (schematic) of a composition of the invention.

If the silica and the liquid are mixed under conditions of a strong shearing in force, the product mixture becomes a wet mass having no fluidity. The reason is supposed as follows. In the case of a composition of this invention, the liquid is divided into small droplets, covered by the silica and separated from each other as shown in FIG. 2 of the accompanying drawings. There is no liquid between such capsules, only air. Therefore, the composition of FIG. 2 can flow freely. In the case of a mixture prepared under mixing conditions of a strong shearing force, however, the silica is dispersed in the liquid and forms a wet mass which cannot flow as freely as the composition of this invention. When the composition is prepared under conditions of a strong shearing force, it changes irreversibly to the wet mass.

Another important factor for carrying out the method of the invention is the order of mixing the silica and the liquid. The silica should be charged into the mixing equipment first and then the liquid should be added onto the silica with mixing. If the silica is added onto the liquid, the purpose of this invention is not achieved. In the technique of adding the liquid, there is no special limitation. However, better results may be obtained by adding the liquid in a form of droplets or of a sprayed mist, especially when the viscosity of the liquid is relatively high.

In mixing temperature, pressure or time there is also no special limitation. Advantageously the method of the invention is carried out at temperatures or pressures below which substantial proportions of the organic liquid will not vaporize. At ordinary ambient temperatures and pressures the method of this invention can be carried out most economically. Mixing time depends on the type and size of equipment used, but normally less than one hour is required. Thus, the method of the invention presents a process for preparing a powdery composition containing a relatively large quantity of organic liquids, such as ethyl alcohol, which is used as a food preservative in a vapor form; liquid fragrances or flavors; pesticides; fungicides or sex pheromones, all of which are used in a vapor form, and still have good fluidity so as to be handled easily in industry. The method of the invention is particularly advantageous for encapsulating biologically active organic liquids such as pesticides and pheromones which are to be controlled in their release over periods of time.

The following examples describe the manner and the process of making and using the invention and set forth the best mode contemplated by the inventor for carrying out the invention. Where reported, the angle of repose of a composition is determined by measurement of the angle made between the surface of the loose, granular or powdery composition and the horizontal after rotation for 2 minutes at 2 r.p.m. in the glass vessel of a Miwa's Rotary Cylinder Type Repose Angle Tester.

EXAMPLE 1

60 kgs of gel type silica, having an average particle size of 100 microns and a pore size distribution wherein 50% of the integrated micropore volume is distributed to micropores having a radius up to 500 Angstroms (Tokusil PR, made by Tokuyama Soda Co., Ltd.) is charged to a 5000 liter, double cone type mixing vessel, which has a showering nozzle inside and is rotatable in a vertical direction. 110 kgs of 98% ethyl alcohol is added onto the silica in the vessel through the showering nozzle while rotating the vessel at a rate of 20 r.p.m. for 30 minutes. After adding the alcohol, the vessel is rotated for another 10 minutes. About 170 kgs of a powdery composition containing about 180 parts alcohol per 100 parts of silica is obtained. The angle of repose of the obtained composition is 43°. The composition flows freely. Repeating the above-described procedure a plurality of times, but varying the proportion of ethyl alcohol added, compositions are obtained with varying angles of repose. The proportions of ethyl alcohol employed (as percentage of loading) and the angles of repose found are given in the FIG. 1 of the accompanying drawings, plotted with the circle symbol along the unbroken line.

EXAMPLE 2

A portion of the composition prepared in Example 1, supra. and having an angle of repose of 43° is subdivided into 1 gm. portions and packed into small polyethylene bags having many small pinholes and heat sealed entirely automatically using an automatic packing machine. There is no trouble with packaging because of the good fluidity. About 100 grams of freshly baked cake and a 1.0 gram bag are packed together in a polyvinylidene chloride coated nylon bag and heat sealed. The baked cake is protected against mold for a month at 25° C., while another portion of the baked cake, packed alone in the same manner described above as a control, molded in a week.

EXAMPLE 3

Example 3 is not an example of the invention but is made for comparative purposes.

20 kgs of the same silica used in Example 1, supra. is charged to a 1500 l, vertical upwardly expanded conical mixing vessel, having a screw agitator. The top end of the shaft thereof circulates while rotating. 36 kgs of 98% ethyl alcohol is showered onto the silica in the vessel under circulation and rotation of the screw shaft for 20 minutes. After addition of the ethyl alcohol, the screw shaft continues to circulate and rotate for an additional 20 minutes. The rate of rotation of the screw shaft is 120 r.p.m. (shear conditions) and circulation is 3 times per minute. The contents become wet and constitute a sticky mass without fluidity.

EXAMPLE 4

20 kgs of the same silica used in comparative Example 3, supra. and 36 kgs of ethyl alcohol are treated using the same mixing equipment used in the comparative Example 3 with the exception that the rate of rotation is 60 r.p.m. (non-shear conditions) and circulation is 1.5 times per minute. After the mixing, about 56 kgs of a powdery composition having an angle of repose of 46° is obtained. Subdivided into 0.6 gram lots, packed and heat sealed as in Example 1, it was used as a food preservative as in the Example 1, supra.

EXAMPLE 5

20 kgs of amorphous gel type silica, having an average particle size of 80 microns and wherein 50% of the integrated micropore volume is distributed to micropores having a radius up to 1000 microns (Tokusil NR, Tokuyama Soda Co., Ltd.) is charged to a 2000 liter V-shaped mixer. The mixer is rotated at the rate of 10 r.p.m. 30 kgs of bouquet type fragrance is then showered onto the silica during rotation for 30 minutes. After that, the mixer is rotated for an additional 5 minutes. About 50 kgs of powdery composition is obtained (angle of repose is 49°). The powder is subdivided into 6 gram portions, packaged and heat sealed as in Example 1, supra. without difficulty. The packages are useful as scented bags.

Repeating the above-described procedure a plurality of times, but using ethyl alcohol as the liquid and varying the proportion of ethyl alcohol added, compositions are obtained with varying angles of repose. The proportion of ethyl alcohol employed (as percentage of loading) and the angles of repose found are given in the FIG. 1 of the accompanying drawings, plotted with the square symbol on the broken line.

EXAMPLE 6

Example 6 is not an example of the invention but is made for comparative purposes.

Figure 1:
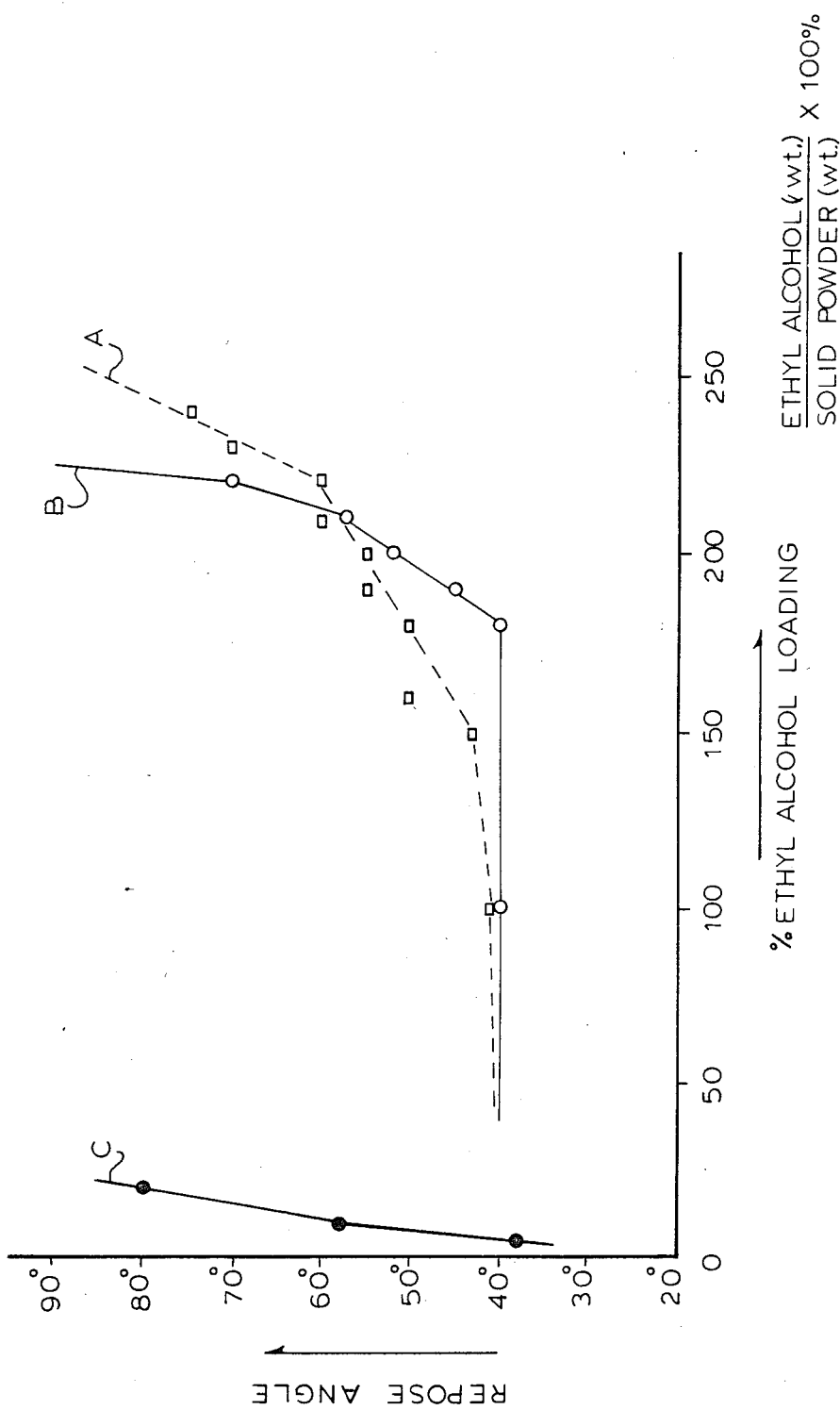
FIG. 1 is a graphical representation of the relationship between liquid loading and the angle of repose obtained for compositions of the invention compared to other capsule compositions.

Repeating the procedure of Example 5, supra. but replacing the silica with aluminum oxide (Sumitomo Chemical Co., Ltd.) and varying proportions of ethyl alcohol, compositions are obtained having unsatisfactory loadings and/or angles of repose as shown in FIG. 1 of the accompanying drawings (plotted with the solid dot on the unbroken line).

EXAMPLE 7

Following the procedure of Example 5, supra., but replacing the bouquet type fragrance with Z-9-hexadecenyl acetate, a free flowing powdery composition composed of Z-9-hexadecenyl acetate encapsulated in silica is obtained, packaged in polyethylene bags. The bag releases vapor of Z-9-hexadecenyl acetate slowly and steadily at a constant rate for about 2 months. It is very useful to control Tea tortrix in a tea garden by the method of insect communication disruption, since Z-9-hexadecenyl acetate is the sex pheromone of the Tea tortrix.

Typical relationships between liquid loading and angle of repose, which is widely recognized as a standard of fluidity of powdery materials, are shown in the FIG. 1. In this FIG. 1 ethyl alcohol is used as the liquid and silica A (Tokusil NR, made by Tokuyama Soda Co., Ltd.), silica B (Tokusil PR, also made by Tokuyama Soda Co., Ltd.) and aluminum oxide C (made by Sumitomo Chemical Co., Ltd.) are used as the powdery solids. For good fluidity, the angle of repose should be smaller than about 50°. From the FIG. 1 it can be seen that silica B (average particle size of 100 micron, 50% of integrated volume of micropore distributed to micropores having a radius up to 500 Angstroms) may be loaded by 180% ethyl alcohol while maintaining a angle of repose at 40° (which means very good fluidity). Silica A (average particle size is 80 micron, 50% of integrated volume of micropore distributed to micropores having a radius up to 1000 Angstroms) may be loaded with 190% ethyl alcohol while maintaining a angle of repose at 55°, which means it has poorer fluidity than silica B loaded by ethyl alcohol, but still has a useful fluidity. To the contrary, aluminum oxide loaded by only 20% ethyl alcohol shows a very high angle of repose (80°), which means it is very resistant to flow and consequently hard to handle.

The relationships shown in FIG. 1 were almost the same when ethyl alcohol was replaced by cis-3-hexenol, a component of fragrance or flavor compositions.

What is claimed:

1. A method of encapsulating a volatile organic liquid having a viscosity of 50 centipoise or less at 25° C., with particles of amorphous silica, which comprises;
providing particles of said silica in a mixing vessel;
adding said liquid to the particles; and
mixing the silica and the liquid under non-shearing conditions; said silica having an average particle size of less than 300 micron and a micropore distribution characterized by 50% of the integrated volume of said micropore being distributed to the micropores having a radius of up to 1000 Angstroms.

2. The product of the method of claim 1.

* * * * *